United States Patent [19]

Hayes et al.

[11] Patent Number: 5,020,519
[45] Date of Patent: Jun. 4, 1991

[54] SAGITTAL APPROXIMATOR

[75] Inventors: S. Kyle Hayes, Warsaw; John E. Meyers, Columbia City; Antony J. Lozier, Warsaw, all of Ind.

[73] Assignee: Zimmer, Inc., Warsaw, Ind.

[21] Appl. No.: 623,470

[22] Filed: Dec. 7, 1990

[51] Int. Cl.⁵ .............. A61B 17/56; A61B 17/58; A61F 5/00
[52] U.S. Cl. ..................... 128/69; 128/20; 606/99; 606/86; 606/104
[58] Field of Search .............. 128/20, 69; 606/86, 606/87, 90, 99, 104

[56] References Cited

U.S. PATENT DOCUMENTS

| | | | |
|---|---|---|---|
| 3,477,429 | 11/1969 | Sampson | 606/86 |
| 4,050,464 | 9/1977 | Hall | 128/303 R |
| 4,147,167 | 4/1979 | Hickmann et al. | 128/20 X |
| 4,269,178 | 5/1981 | Keene | 128/69 |
| 4,271,836 | 6/1981 | Bacal et al. | 128/303 R |
| 4,409,968 | 10/1983 | Drummond | 128/69 |
| 4,411,259 | 10/1983 | Drummond | 128/69 |
| 4,422,451 | 12/1983 | Kalamchi | 128/69 |
| 4,641,636 | 2/1987 | Cotrel | 128/69 |
| 4,815,453 | 3/1989 | Cotrel | 128/69 |
| 4,927,425 | 5/1990 | Lozier | 606/99 |
| 4,932,395 | 6/1990 | Mehdizadeh | 128/20 |

FOREIGN PATENT DOCUMENTS 0348272 12/1989 European Pat. Off. .

OTHER PUBLICATIONS

Stuart, Inc. Literature-Universal Instrumentation (CD) for Spinal Surgery-Dr. Cotrel/Dr. Dubousset-1985, pp. 1-19.

Primary Examiner—Richard J. Apley
Assistant Examiner—Karen G. Horowitz
Attorney, Agent, or Firm—Margaret L. Geringer

[57] ABSTRACT

A sagittal approximator for clamping engagement with an open back hook for urging a spinal rod into seating engagement with said hook. The sagittal approximator includes an integral fixed handle and jaw. A shiftable handle is pivotally connected to the fixed handle. A shiftable jaw is pivotally connected to the fixed handle adjacent the fixed jaw. The pivotal handle and jaw are pivotally interconnected such that as the pivotal handle is shifted, the pivotal jaw shifts accordingly. The fixed handle includes a threaded channel and longitudinal guide rib. A spinal rod engagement head is slidably carried by the fixed handle and jaw and includes a spinal rod seat which with contact with the spinal rod produces a balanced seating load on the rod. A threaded pusher rod is carried by the channel which when rotated longitudinally shifts the head relative to the fixed handle.

7 Claims, 4 Drawing Sheets

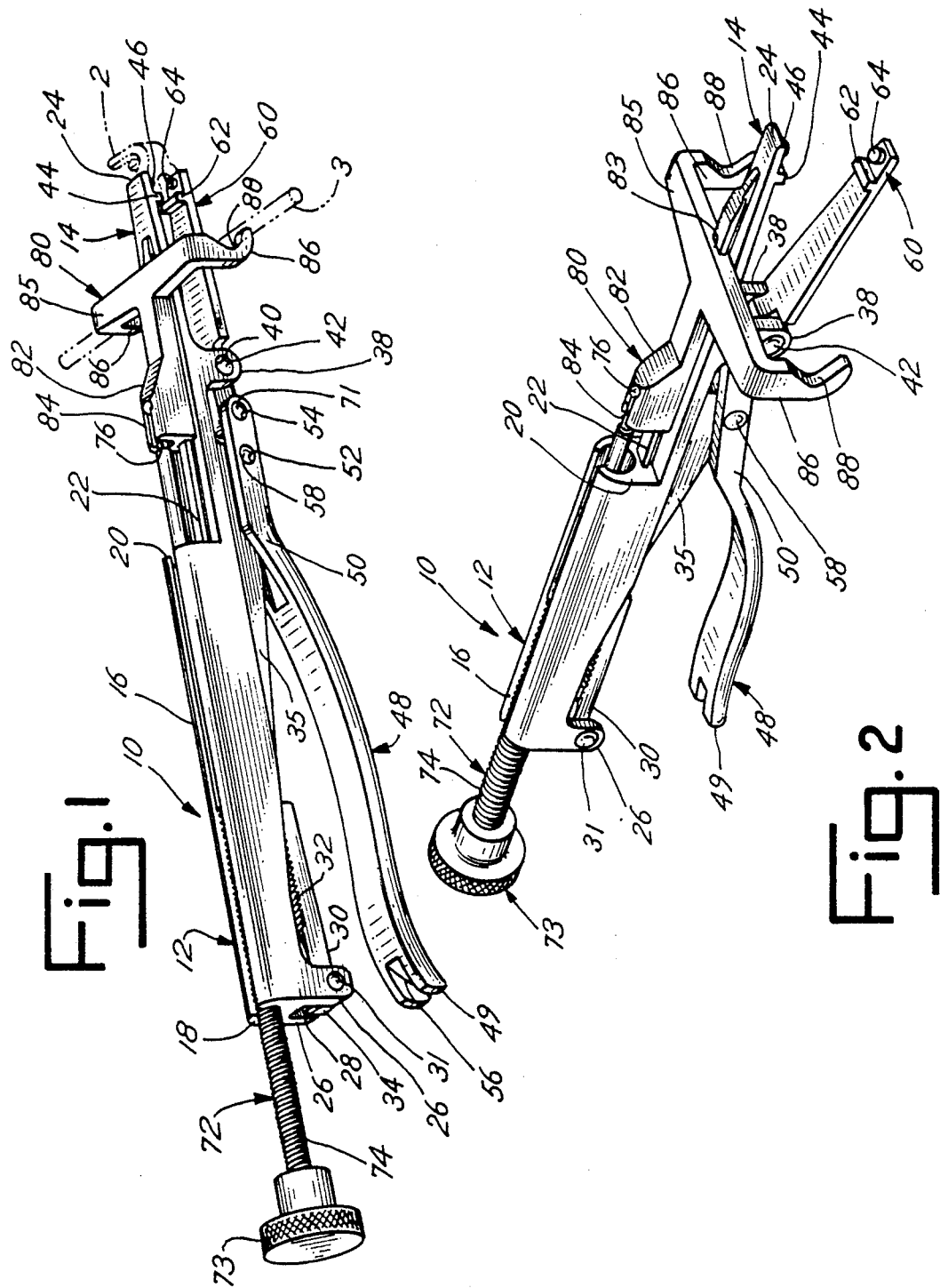

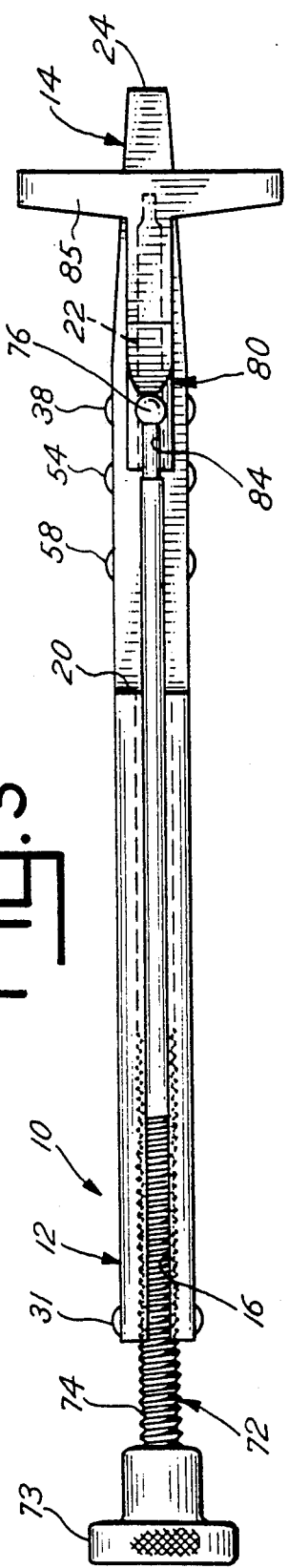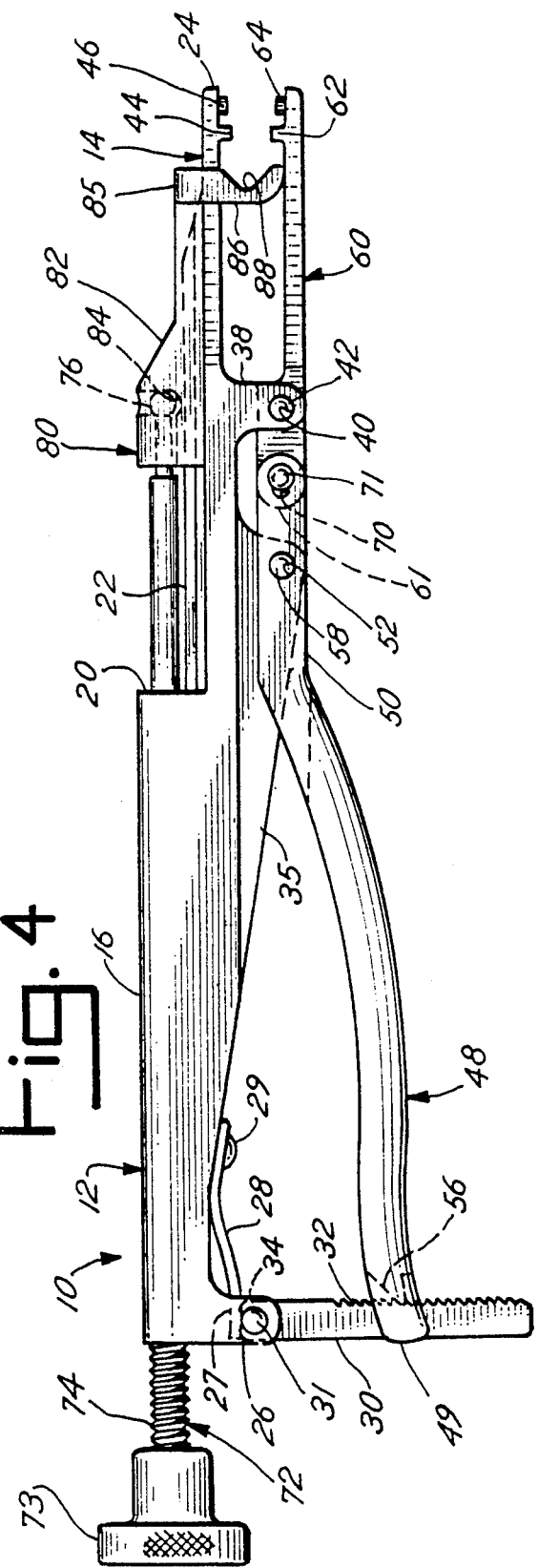

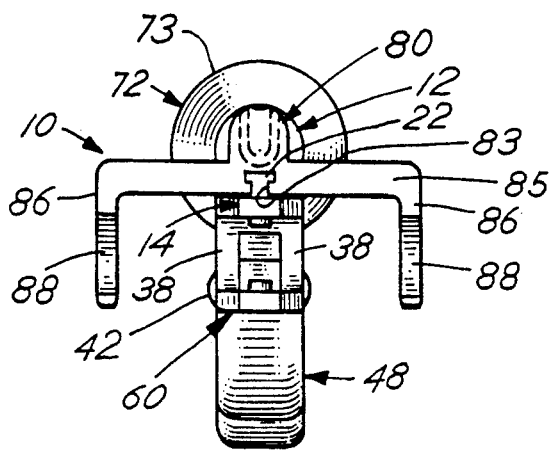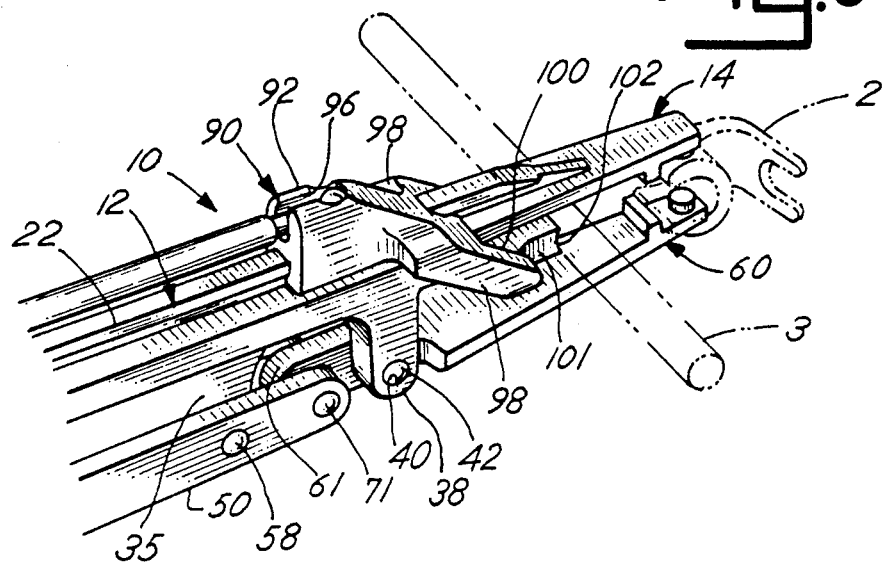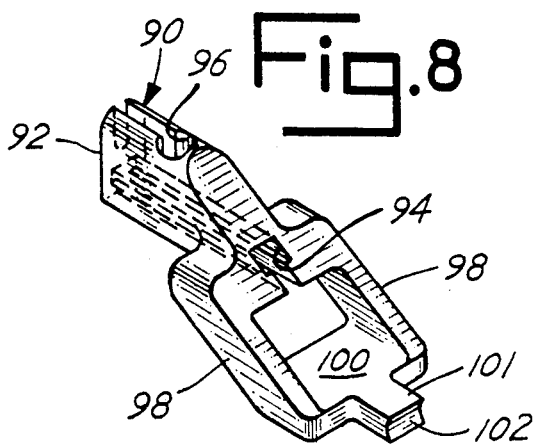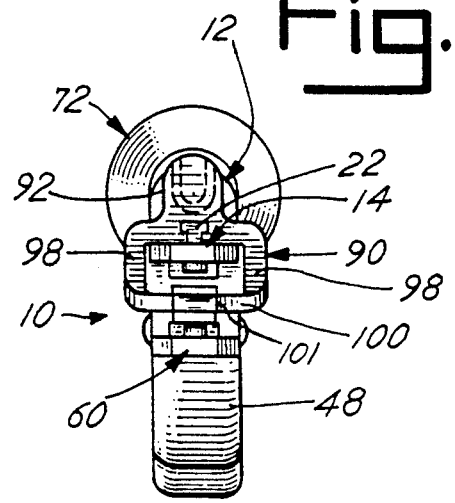

SAGITTAL APPROXIMATOR

FIELD OF THE INVENTION

This application relates to a sagittal approximator for seating a spinal rod into an open back hook during a posterior spinal fixation procedure.

BACKGROUND OF THE INVENTION

During a posterior spinal fixation procedure a plurality of metal rods may be connected by the surgeon to the spinal column of a patient by a series of open back hooks or other spinal fixation devices. The rods are connected to the open back hooks and follow the curvature of the patient's spine. An example of an open back hook may be had by reference to U.S. Pat. Nos. 4,269,178 and 4,815,453, although such hooks are not limited thereto. An open back spinal hook may be any suitable spinal hook having a slot-type opening into the body of the hook, enabling an elongated spinal rod to pass through the slot for seating arrangement with the hook. The subject matter of the referenced patent numbers is provided solely to provide an understanding of the environment for the invention and in no way should be considered limiting.

Generally the rods are inserted into the open back hooks by applying pressure to the rod using a rod pusher as illustrated in U.S. Pat. No. 4,927,425. However, it is not uncommon for additional force or stability to be required to seat the rod within the open back hook. In such cases, a surgeon attaches a clamp to the hook and uses a mechanical device, such as the rod pusher, to seat the rod.

It is considered most convenient if the clamp and rod pusher or introducer are interconnected. An example of such a combination hook clamp and rod introducer is manufactured by Stuart, Inc. of Greensburg, Pa. and sold under the designations 84609 Bulb hook holder and 84607 rod introducer. In the Stuart device the rod introducer includes a partially threaded screw shaft having a swivel head connected at one end for contacting the rod and a wing nut connected at its opposite end. When connected to the bulb hook holder, the screw shaft with the swivel head attached is laterally spaced from the jaws of the holder. As the screw shaft of the rod introducer is rotated, the head pushes the rod into the hook stabilized by the clamp or holder. In use, the offset orientation of the swivel head relative to the jaw causes a moment arm to be established as the spinal rod is seated into the hook. Further, even after connection of the introducer to the holder, the introducer may be rotatable about a lateral axis of the shaft relative to the holder. The rotation about the lateral axis of the shaft in combination with the offset screw shaft presents an awkward tool for the surgeon.

SUMMARY OF THE INVENTION

The device of this invention hereinafter referred to as a sagittal approximator eliminates the problems associated with the prior art device described above by laterally aligning the head of the rod introducer with the clamp jaws. The clamp part or holder of the invention includes a fixed jaw and handle top combination and a shiftable jaw connected to the fixed handle by a double hinge. A pusher rod is threadably accommodated by a channel formed along the top of the rear portion of the fixed handle. A thumb wheel is connected at one end of the pusher rod. The rod terminates at its opposite end in a bulbous tip. A T-shaped rib is formed along the top of the fixed handle and extends from the end of the channel toward the tip end of the fixed jaw. A rod engaging head is removably connected to the bulbous tip of pusher rod and includes a T-shaped channel for slidably accommodating the T-shaped rib. As the pusher rod is rotated in one direction within the threaded channel, the head is slid along the top of the fixed jaw guided by the rib toward the jaws of the sagittal approximator. The head includes a rod engaging member which contacts the spinal rod and forces it into seating arrangement with an open back hook. Since the head and pusher rod is laterally aligned with the clamp, the load on the spinal rod is balanced at the center of the hook. Further the direct connection of the pusher rod and head to the clamp provides a one piece clamp and rod introducer eliminating a great deal of awkwardness associated with prior art two piece devices.

Accordingly, it is an object of this invention to provide for a novel sagittal approximator.

Another object of this invention is to provide for a novel open back hook holder.

Another object of this invention is to provide for a novel open back hook holder having a rod introducer connected thereto in lateral alignment with the holder.

Another object of this invention is to provide for a sagittal approximator wherein the force exerted on a rod is centered relative to the open back hook.

Other objects of this invention will become apparent upon a reading of the following description taken with the accompanying drawings.

BRIEF DESCRIPTION OF THE DRAWINGS

FIG. 1 is a perspective view of the invention with a hook and rod shown in broken lines for illustrative purposes only.

FIG. 2 is a reverse perspective view of the invention.

FIG. 3 is a top elevational view of the invention.

FIG. 4 is a side elevational view of the invention.

FIG. 5 is a front end elevational view of the invention.

FIG. 6 is a fragmented perspective view of the invention having an alternative embodiment of the rod engaging head with a rod and hook shown in broken lines for illustrative purposes.

FIG. 7 is a front end elevational view of FIG. 6.

FIG. 8 is a perspective view of the alternative embodiment of the rod engaging head shown in use in FIG. 6.

DESCRIPTION OF THE PREFERRED EMBODIMENTS

Figure 9:
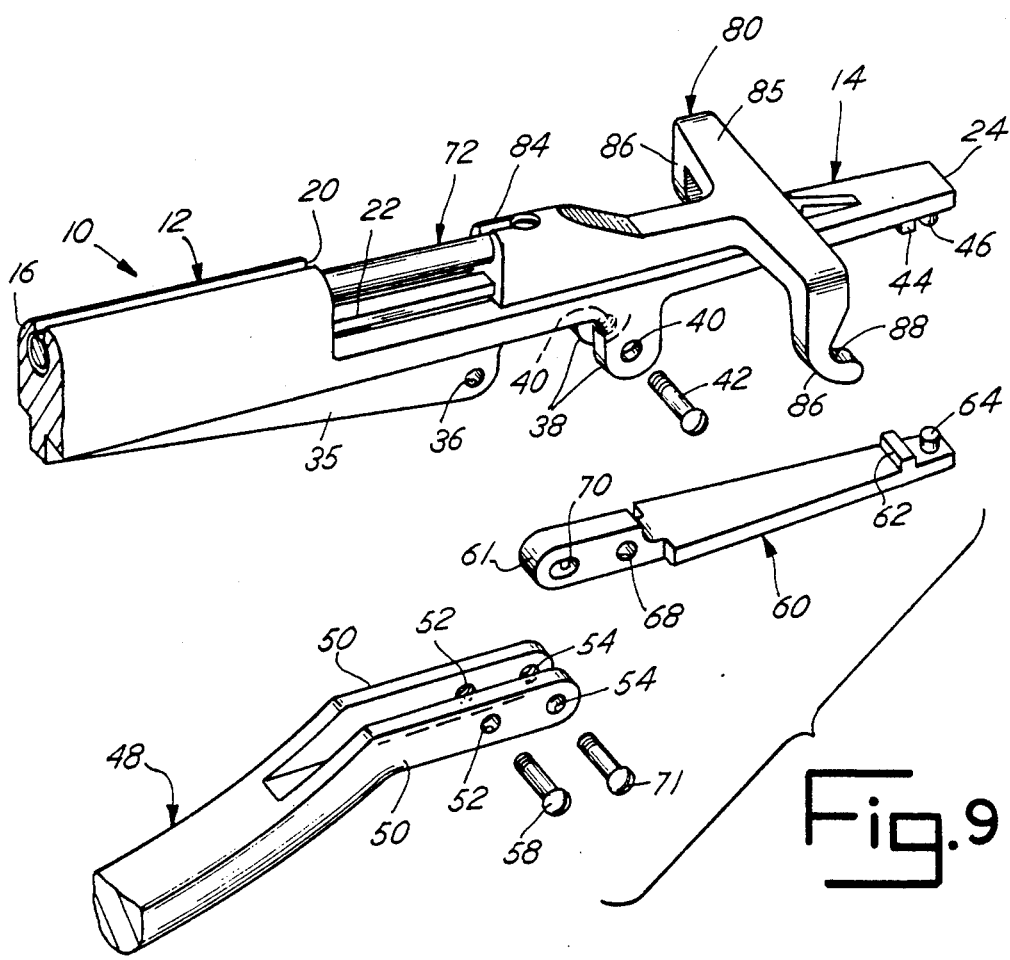
FIG. 9 is an exploded fragmented view of the invention of FIGS. 1-5.

The preferred embodiments herein disclosed are not intended to be exhaustive or to limit the invention to the precise forms disclosed. Rather, they are chosen and described so that others skilled in the art may utilize its teachings.

Referring now to the drawings, sagittal approximator 10 includes a fixed handle 12 having an integral fixed upper jaw 14. A generally C-shaped channel 16 is formed in the upper surface of handle 12. Channel 16 extends from end 18 of handle 12 toward jaw 14 and terminates abruptly forming an abutment 20. Channel 16 in the preferred embodiment is partially threaded as shown. A T-shaped guide 22 extends along the top surface of handle 12 from abutment 20 toward jaw part 14 and terminates in a sloped end spaced from the jaw end 24. A pair of spaced legs 26 extend downwardly from the underside of fixed handle 12 adjacent end 18. Each leg 26 includes a bore formed therethrough with one of the bores including threads. A leaf spring 28 is connected to the underside of fixed handle 12 by a fastener 29. The free end 27 of spring 28 extends between legs 26. A rack 30 is shiftably connected to legs 26 by a fastener 31 and includes a generally squared end 34. Square end 34 of rack 30 in combination with leaf spring 28 imparts a positive snap feel to rack 30 when pivoted toward the position of FIG. 4. Rack 30 may be collapsed to lie adjacent the underside of handle 12 as shown in FIGS. 1 and 2. Rack 30 includes a plurality of teeth 32. A flange 35 extends downwardly from the underside of handle 12 and includes a bore 36 formed therethrough (see FIG. 4). A pair of spaced legs 38 extend downwardly from the underside of handle 12 as illustrated and each include a through bore 40 therethrough in alignment with one another. Legs 38 are longitudinally spaced from flange 35. One of the bores formed in one leg 38 includes threads for accommodating a fastener 42. Fixed jaw 14 includes a transverse abutment 44 extending downwardly from the jaw and a tooth 46 adjacent end 24 of the jaw 14.

A lower handle 48 is provided and includes a pair of spaced legs 50 each including a bore 52 therethrough for accommodating a fastening device. One of the bores 52 include threads. Each leg includes a second bore 54 adjacent the end of the leg with one of the bores 54 including threads. The opposite end of handle 48 includes a single tooth 56 inset relative the handle end 49 for engagement with the teeth 32 of rack 30. A fastener 58 is threadably accommodated by bores 52 of legs 50 and extends through bore 36 of flange 35 to pivotally connect handle 48 to fixed handle 12.

A lower jaw 60 is pivotally connected to fixed handle 12 at legs 38 by a fastener 42 extending through bore 68 of the lower jaw 60 and bores 40 of legs 38. Lower jaw 60 includes an upwardly extending transverse abutment 62 and a tooth 64. Jaw 60 is connected to handle 12 such that its tooth 64 is aligned with tooth 46 of fixed jaw 14 and its abutment 62 is aligned with abutment 44 of jaw 14 when the jaws are substantially parallel (see FIG. 4). A slotted bore 70 is formed through jaw 60 near end 61. A fastener 71 extends through bores 54 of handle legs 50 and slotted bore 70 of jaw 60 to pivotally connect pivotable handle 48 to pivotal jaw 60. Due to the pivotal connection of lower handle 48 and of lower jaw 60 to fixed handle 12, as well as their pivotal interconnection by fastener 71 three pivot points are established about fasteners 58, 42 and 71 respectively. The use of three pivot points provide a tool wherein the top jaw 14 and handle 12 are stationary and the lower jaw 60 pivots about fastener 42 responsive to pivotal movement of handle 48. As the handle 48 and jaw 60 pivot, fastener 71 slides within slotted bore 70 of jaw 60.

An introducer rod or pusher rod 72 is threadably accommodated by channel 16 and includes a threaded portion 74 and bulbous end 76. A thumb wheel 73 is connected to rod 72 adjacent threaded portion 74. A portion of the shaft of rod 72 along with the bulbous end 76 extends outwardly from channel 16 toward jaw 14. Bulbous end 76 of rod 72 is laterally aligned with T-shaped guide 22 being spaced parallel and above the guide as shown. As rod 72 is rotated within channel 16 the rod is longitudinally shifted along the channel by the threaded engagement between the rod and channel.

A spinal rod engaging head 80 is provided and includes a body 82 having a T-shaped channel 83 formed in the bottom of the head (see FIG. 5). A slot 84 having a bulbed end is formed in the upper surface of head 80 and extends rearwardly as shown. Head 80 further includes a transverse body part 85. A leg 86 extends downwardly from each end of part 85 as illustrated. Each leg includes a recessed spinal rod seat 88.

In use, a head 80 is connected to sagittal approximator 10 such that T-shaped guide 22 slides within channel 83 of the head. End 76 of rod 72 is seated within slot 84. The bulbed end of push rod 72 permits rotation of the rod relative to head 80 but prevents the head from shifting longitudinally relative to the push rod 72. Thumb wheel 78 is turned by the surgeon in one direction to draw rod 72 and head 80 rearwardly or turned in the opposite direction to shift the rod and head forwardly. Abutment 20 defines the fully rearward position of head 80.

The surgeon seats tooth 46 of fixed jaw 14 into alignment bore of the body of the spinal hook 2 shown in broken lines in FIG. 1. End 49 of handle 48 is drawn toward fixed handle 12 to pivot jaw 60 toward fixed jaw 14 until tooth 64 of the pivotal jaw seats within a second alignment bore of the body of the hook. Slight manipulation may be required to seat the jaw teeth properly. Once the teeth are seated, the surgeon squeezes handle 48 to further draw end 49 toward handle 12 to clamp the hook between the jaws. If desirable, rack 30 may be extended prior to seating of the teeth within the hook, such that as end 49 of handle 48 is pivoted toward handle 12, tooth 56 engages with the rack teeth to temporarily fix handle 48 relative to handle 12 when sufficient clamping pressure is exerted on the hook by the jaws.

When the jaws 14 and 60 are clamped to the hook 2, as described, a spinal rod or section of a spinal rod 3 used in the procedure is positioned between the jaws. FIG. 1 illustrates the positioning of spinal rod 3 relative to jaws 14 and 60 wherein spinal rod 3 is illustrated in broken lines only. The head 80 is positioned such that spinal rod 3 is between the hook 2 and head 80 (see FIG. 1).

To seat spinal rod 3 within the open back hook 2, the user rotates thumb wheel 73 to shift pusher rod 72 longitudinally along handle 12 toward jaw 14. Rod 72 slides head 80 along T-shaped guide 22. As head 80 is slid toward hook 2 by pusher rod 72, legs 86 of the head contact spinal rod 3 at seats 88 of the legs to urge the spinal rod toward the hook. Continued rotation of thumb wheel 73 pushes the head and spinal rod toward the hook. When the spinal rod reaches the hook, additional rotation of the thumb wheel forces the spinal rod through the opening in the hook 2 and into seating arrangement with the hook. Since a leg 86 extends downwardly on each side of the jaw the spinal rod is engaged on each side of hook 2, and thus the legs 86 of head 80 straddle the hook. The load on the spinal rod is balanced or centered relative to the hook 2 to cause an even seating of the spinal rod and prevent a moment arm from developing on the spinal rod.

An alternative embodiment of the spinal rod contacting head is illustrated in FIGS. 6–8. Spinal rod contacting head 90 includes a body 92 having a T-shaped channel 94 and a bulbous slot 96 similar to head 80. A pair of legs 98 extend at a downward angle from body 92 and are integral with an interconnecting end wall 100. A protrusion 101 extends longitudinally from wall 100 and includes an arcuate seat 102 for engaging the spinal rod. As illustrated in FIGS. 6 and 7 when head 90 is connected to sagittal approximator 10 previously described, end wall 100 and protrusion 101 are positioned between jaws 14 and 60. In use, protrusion 101 contacts a spinal rod and seats the spinal rod into the hook as the thumb wheel 78 is rotated. Protrusion 101 is centrally aligned with the jaws which aligns the force on the rod with the center of the body of the hook to balance the load on the spinal rod to evenly seat the spinal rod within the hook.

The choice of which head 80 or 90 to be used during the procedure is primarily one of surgeon's preference. However, it may be especially useful to use head 90 when an insufficient length of rod extends from one end of the hook as may be commonly experienced near either the end of the patient's spine. The heads 80 or 90 may be conveniently interchangeably connected to the sagittal approximator instrument.

It should be understood that the invention is not to be limited to the precise forms disclosed but may be modified within the scope of the appended claims.

We claim:

1. A surgical device for clamping engagement with a spinal fixation hook and for urging a spinal rod into seating engagement with the clamped hook, the hook having a body having a slot therein for accommodating the rod, said device including a clamp having a fixed handle with integral fixed jaw, a shiftable jaw and a shiftable handle being pivotally connected to said fixed handle and jaw, wherein as said shiftable handle pivots toward said fixed handle said pivotal jaw pivots toward said fixed jaw for clamping engagement with said body of the hook positioned between the jaws, said device further including an engagement means slidably carried by said fixed handle adapted for engagement with said spinal rod to urge said spinal rod through said slot and into seating engagement with said body of the hook, said engagement means being longitudinally shiftable along an upper surface of said fixed handle and jaw between a retracted position and an extended position relative to said fixed jaw, and a shifting means connected to said engagement means and carried by said fixed handle for longitudinally shifting said engagement means.

2. The surgical device of claim 1 further including a longitudinal guide formed along a portion of said upper surface, said engagement means including a body slidably accommodating said guide to shiftably connect said engagement means to said fixed handle and jaw, a pair of legs extend from said body on opposite side edges of said fixed jaw, seat means carried by said legs for contacting said spinal rod as said engagement means is shifted from said retracted position toward said extended position.

3. The surgical device of claim 2 wherein said seat means is vertically aligned between said fixed jaw and said pivotal jaw such that contact with said spinal rod causes a load on said spinal rod to be laterally aligned with a longitudinal axis of said surgical device.

4. The surgical device of claim 1 further including a threaded channel formed in said fixed handle, said shifting means including a shaft threadably accommodated by said channel, wherein as said shaft is rotated within said channel said shaft longitudinally shifts relative to said channel, said shaft including an end rotatably connected to said engagement means, wherein rotation of said shaft in one direction causes said shaft to longitudinally shift relative to said fixed handle to shift said engagement means toward said extended position.

5. A surgical device for clamping to an open back hook and seating a spinal rod within said hook, said device comprising a clamp having an integral stationary first handle part and stationary first jaw part, a second jaw part pivotally connected at its proximal end to said first jaw part, a second handle part pivotally connected at its proximal end to said first handle part, said proximal end of second jaw part and said proximal end of second handle part being pivotally interconnected, said second jaw part having a distal end, said second handle part having a distal end, wherein as said distal end of said second handle par is pivoted toward said stationary first handle part said distal end of second jaw part is pivoted toward said stationary first jaw part.

6. In combination a spinal rod engaging head and a sagittal approximator said sagittal approximator including an integral fixed handle and jaw part having a guide rib formed on its upper surface, said head including a body having a channel being formed therein for slidable accommodation of said guide rib, a pair of legs extend downwardly from said body on opposite sides of said channel, said legs carrying seat means for engagement with said spinal rod.

7. The spinal rod engaging head of claim 6 wherein said seat means includes a wall extending between said legs, a protrusion extends outwardly from said wall in a direction away from said body, said protrusion includes an arcuate end.

* * * * *